(12) United States Patent
Miyazaki et al.

(10) Patent No.: US 10,067,152 B2
(45) Date of Patent: Sep. 4, 2018

(54) AUTOMATIC ANALYZER

(71) Applicant: HITACHI HIGH-TECHNOLOGIES CORPORATION, Tokyo (JP)

(72) Inventors: Masaru Miyazaki, Tokyo (JP); Takamichi Mori, Tokyo (JP); Kazuhiro Nakamura, Tokyo (JP); Isao Yamazaki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 16 days.

(21) Appl. No.: 15/111,006

(22) PCT Filed: Jan. 13, 2015

(86) PCT No.: PCT/JP2015/050699
§ 371 (c)(1),
(2) Date: Jul. 12, 2016

(87) PCT Pub. No.: WO2015/111469
PCT Pub. Date: Jul. 30, 2015

(65) Prior Publication Data
US 2016/0334432 A1 Nov. 17, 2016

(30) Foreign Application Priority Data

Jan. 24, 2014 (JP) ................. 2014-011487

(51) Int. Cl.
*G01N 35/10* (2006.01)
*G01N 21/75* (2006.01)
*G01N 35/04* (2006.01)

(52) U.S. Cl.
CPC ......... *G01N 35/1004* (2013.01); *G01N 21/75* (2013.01); *G01N 2035/0453* (2013.01)

(58) Field of Classification Search
CPC .................................................. G01N 35/1004
See application file for complete search history.

(56) References Cited

U.S. PATENT DOCUMENTS

| 5,186,194 A * | 2/1993 | Kitajima | G01N 35/1004 134/154 |
| 2015/0346231 A1* | 12/2015 | Mori | G01N 35/1004 422/67 |

FOREIGN PATENT DOCUMENTS

| EP | 2 407 791 A1 | 1/2012 |
| JP | 53-57893 U | 5/1978 |

(Continued)

OTHER PUBLICATIONS

International Preliminary Report on Patentability received in corresponding International Application No. PCT/US2015/050699 dated Aug. 4, 2016.

(Continued)

*Primary Examiner* — P. Kathryn Wright
(74) *Attorney, Agent, or Firm* — Mattingly & Malur, PC

(57) ABSTRACT

An automatic analyzer has a washing tank providing water for washing a reagent or sample probe is. The washing water from a washing nozzle spreads from a throttle portion and is divided into right and left flows after colliding with a vent plate provided in an overflow portion of the washing tank. The washing water flows between the vent plate and the inner wall of the overflow portion, and the flows join behind the vent plate. After joining, the washing water flows downward along the vent plate and the inner wall of the overflow portion and then is drained. Because a space is created between the washing water which has collided with the vent plate and the washing water joined behind the vent plate, the washing water is prevented from completely covering the overflow portion, and the airflow can be secured during the drainage.

9 Claims, 10 Drawing Sheets

(56) References Cited

FOREIGN PATENT DOCUMENTS

| | | |
|---|---|---|
| JP | 04-105066 A | 4/1992 |
| JP | 2001-133466 A | 5/2001 |
| JP | 2002-340913 A | 11/2002 |
| JP | 2003-088812 A | 3/2003 |
| JP | 2005-257491 A | 9/2005 |
| WO | 2014/112591 A1 | 7/2014 |

OTHER PUBLICATIONS

International Search Report of PCT/JP2015/050699 dated Apr. 21, 2015.
Extended European Search Report received in corresponding European Application No. 15740752.9 dated Aug. 29, 2017.

* cited by examiner

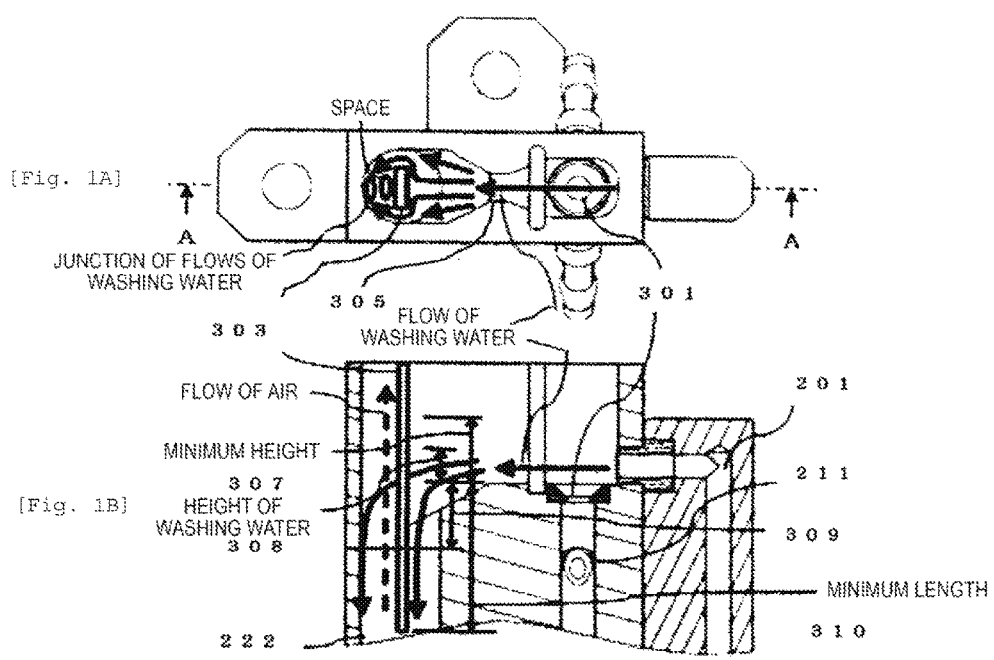
[Fig. 1A]
[Fig. 1B]
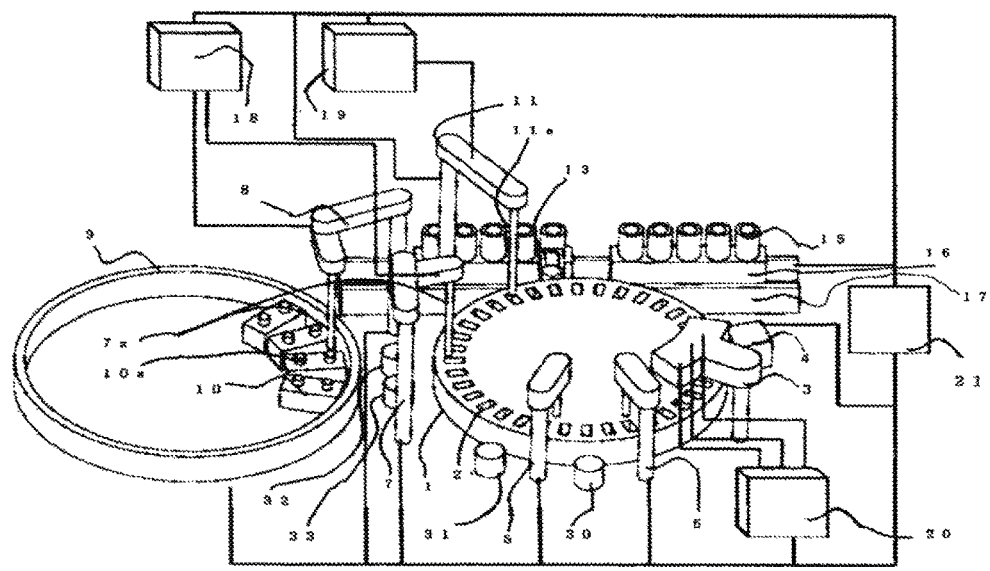
[Fig. 2]

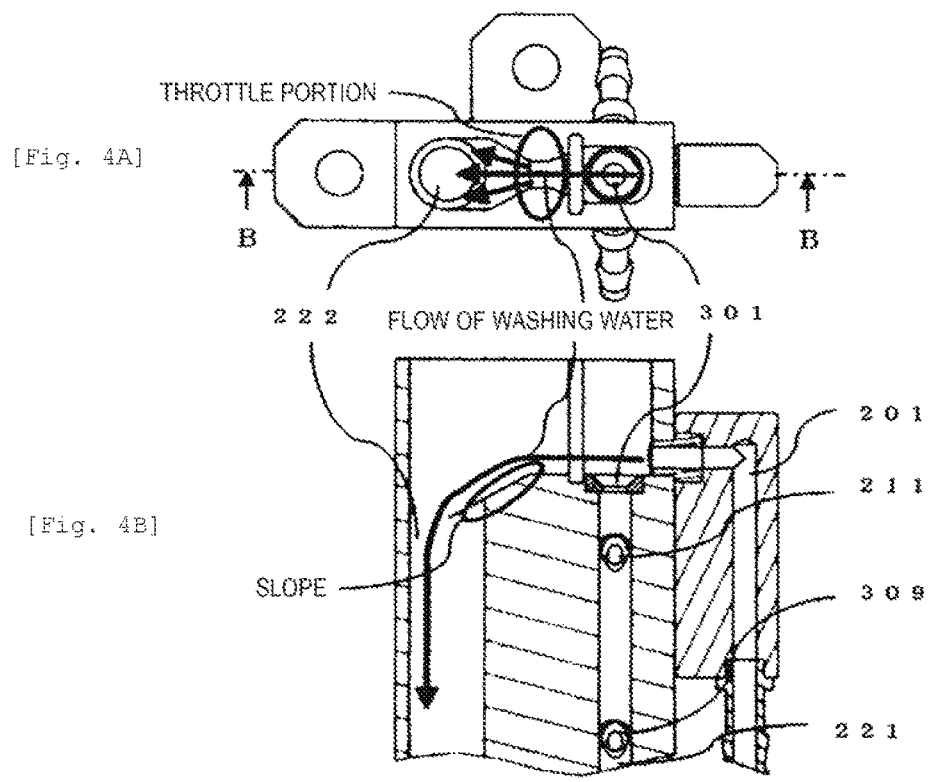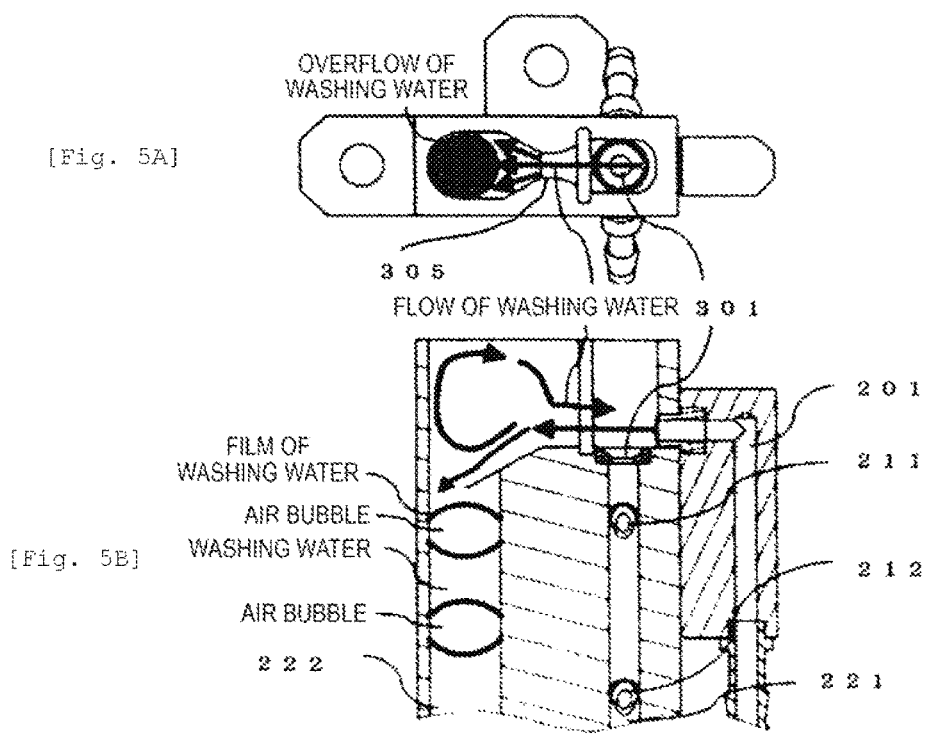

[Fig. 6]
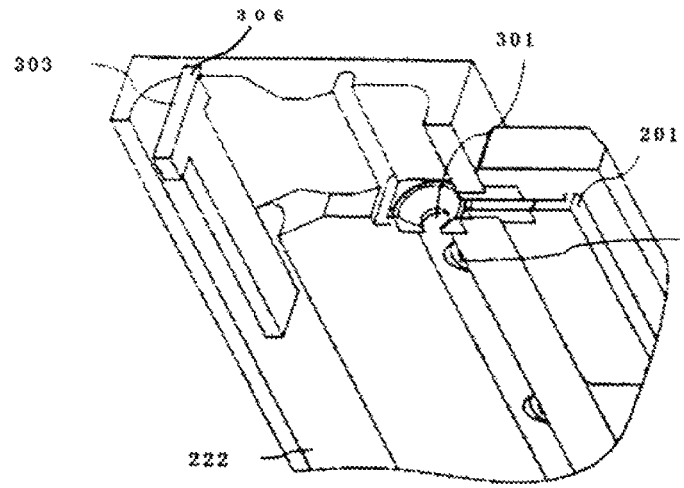
[Fig. 7A]
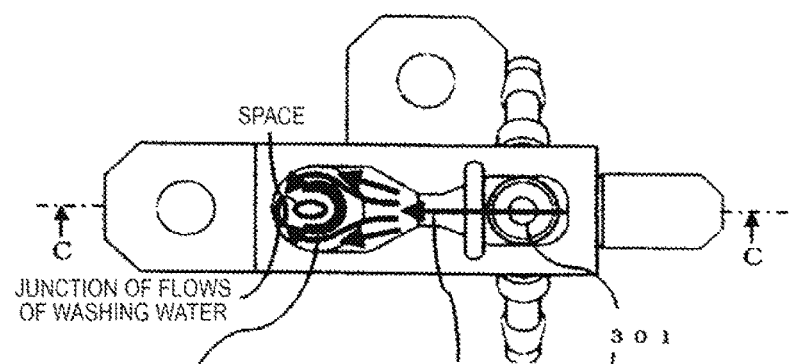
[Fig. 7B]
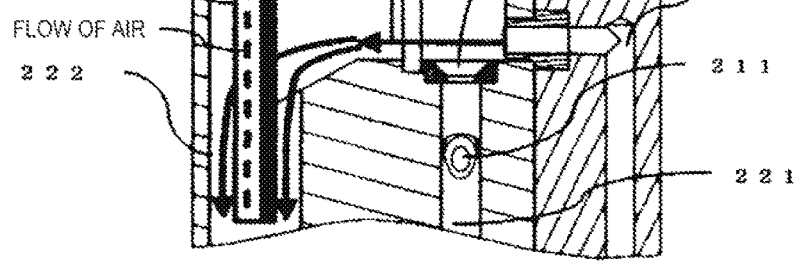

[Fig. 8]
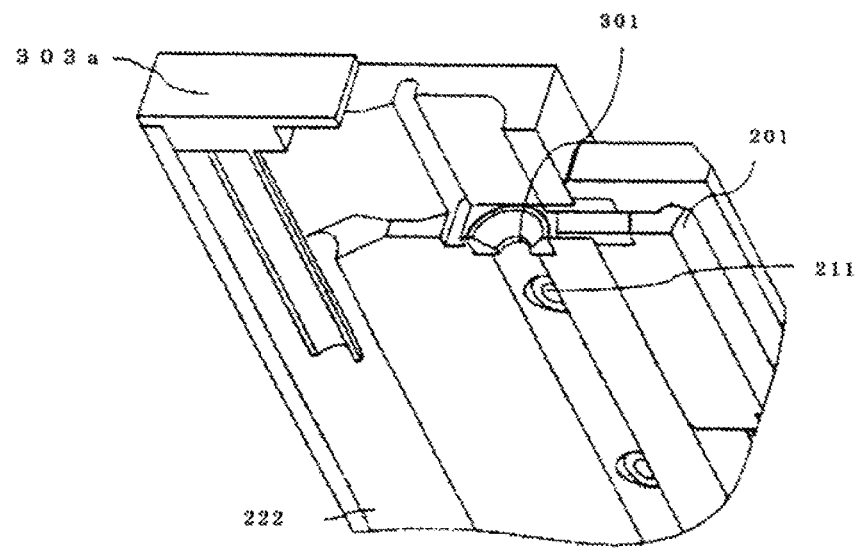
[Fig. 9A]
[Fig. 9B]
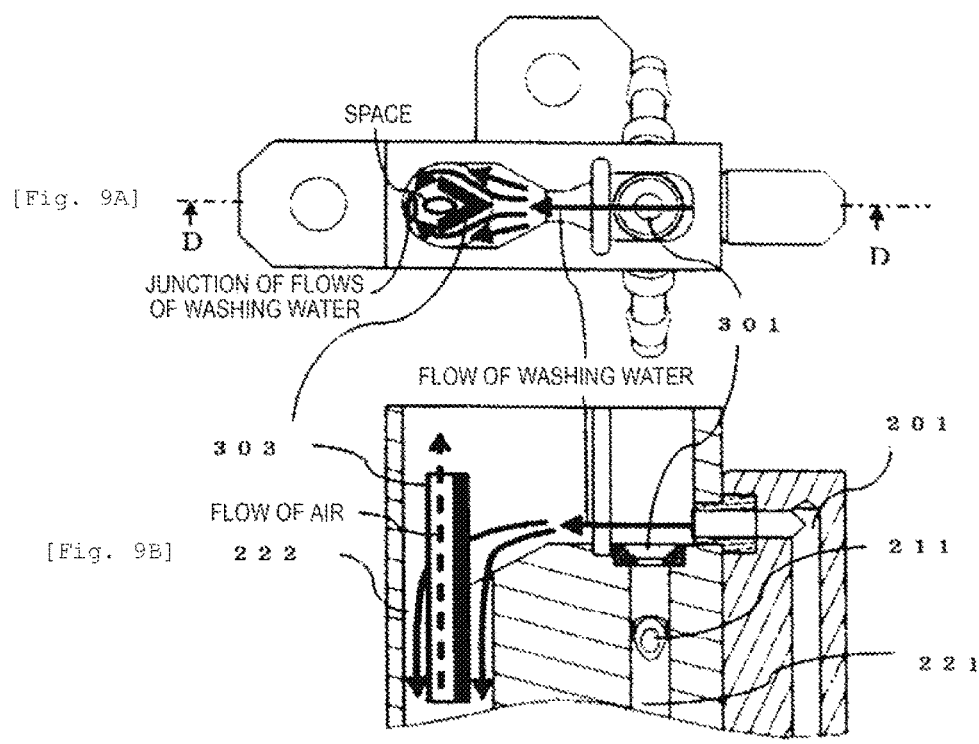

[Fig. 10]
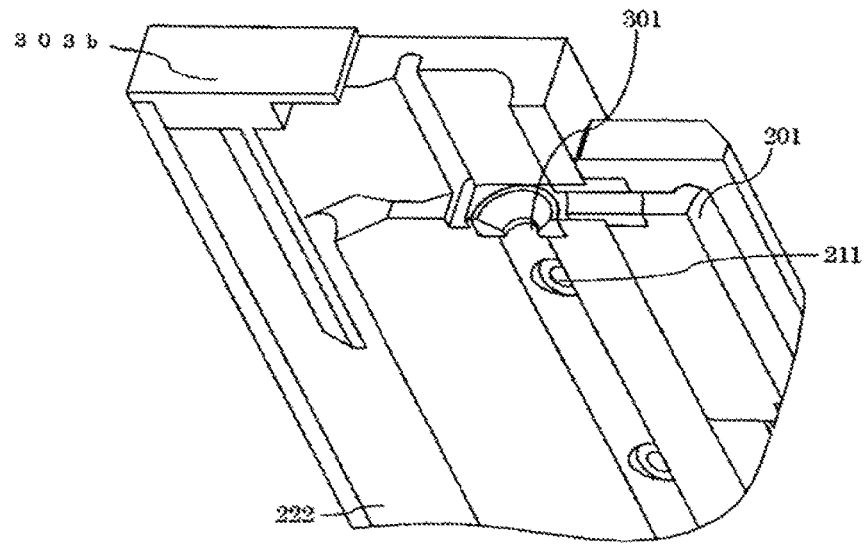
[Fig. 11A]
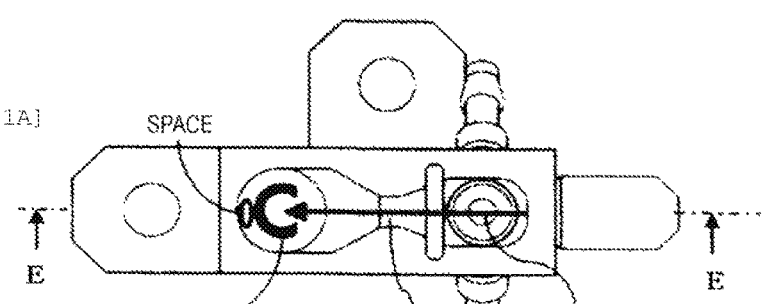
[Fig. 11B]
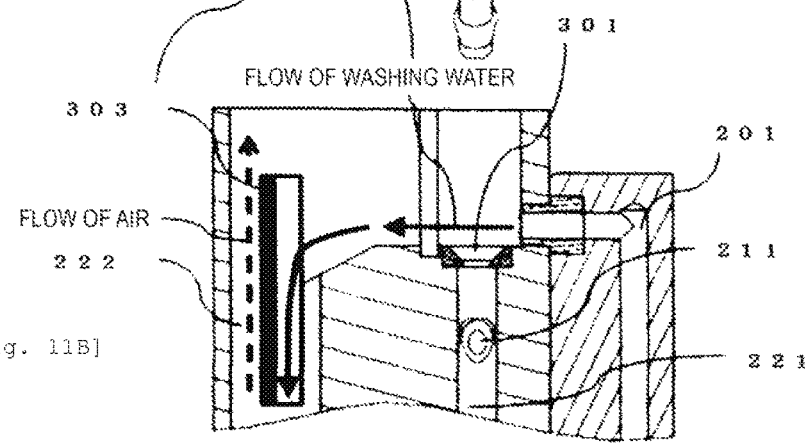

[Fig. 12]
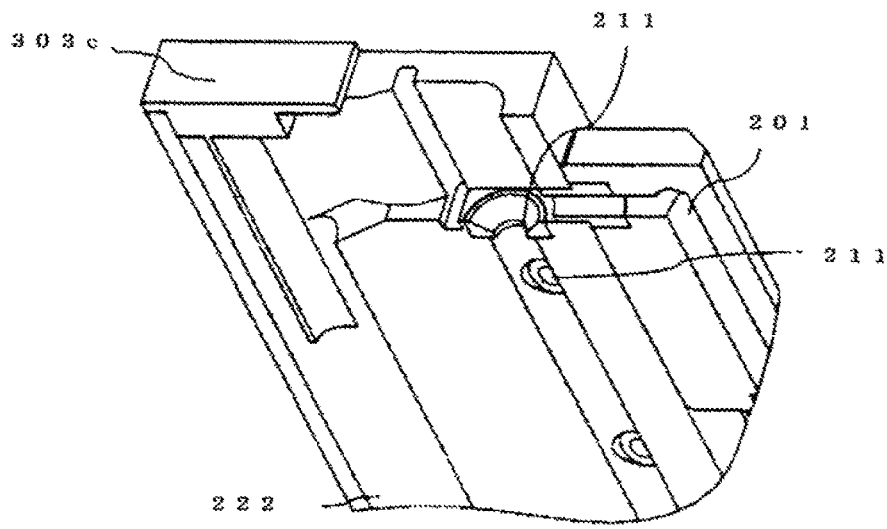
[Fig. 13A]
[Fig. 13B]
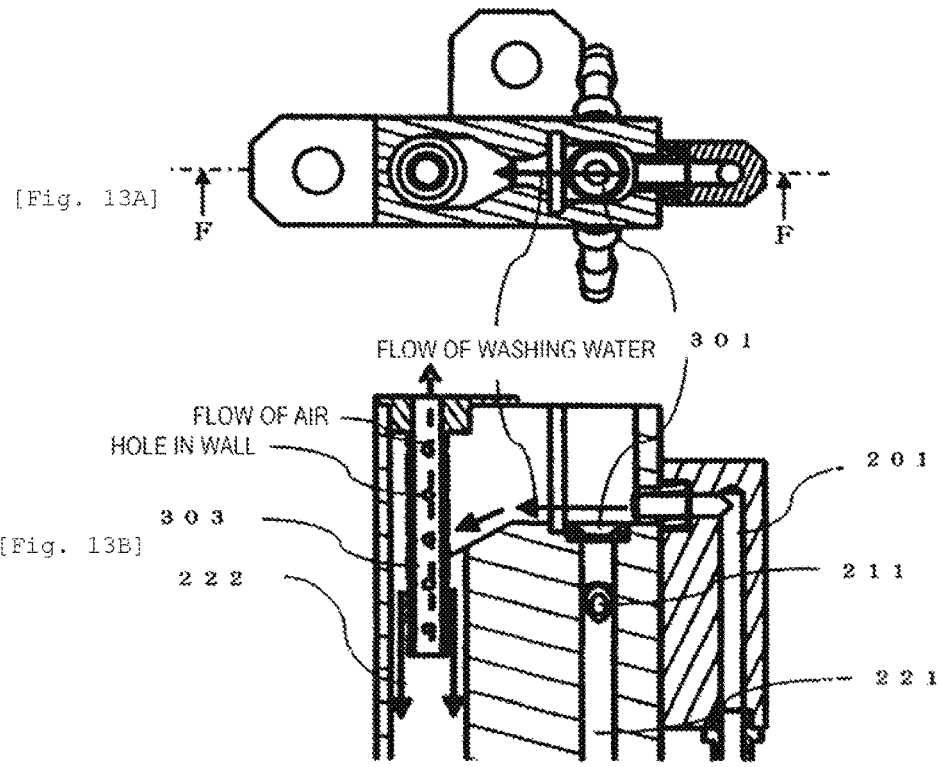

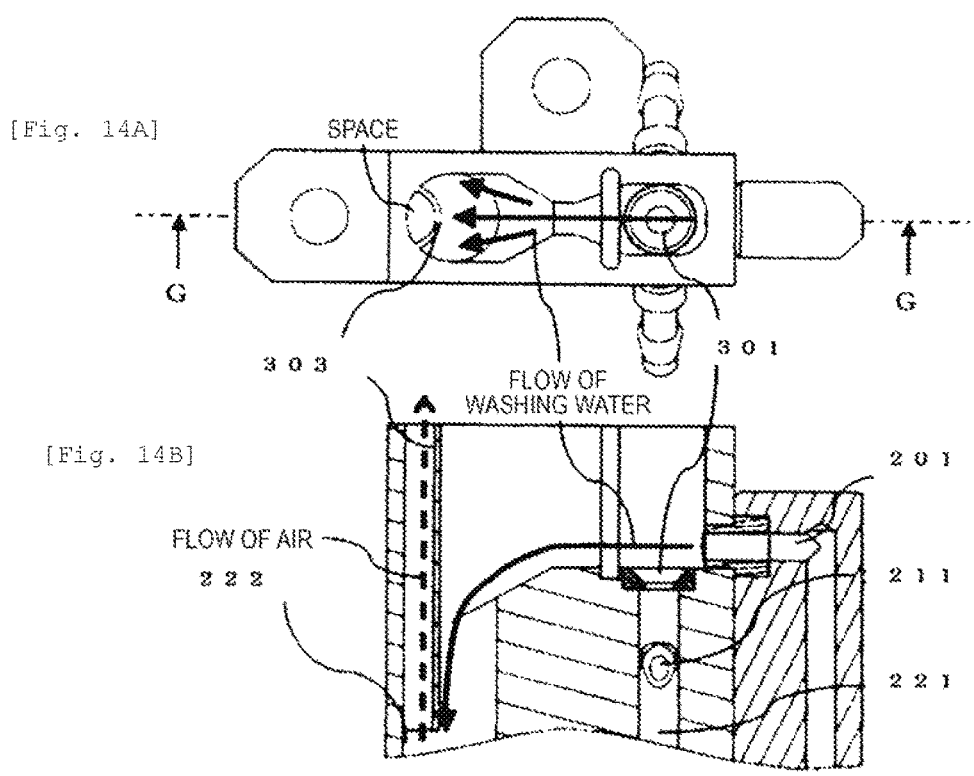

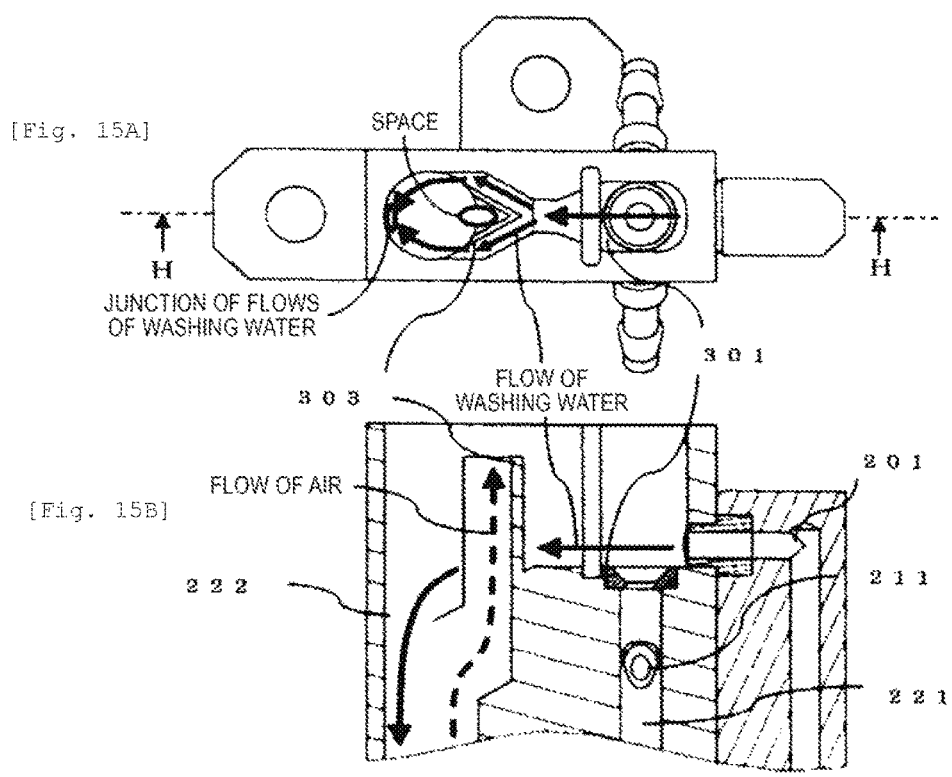

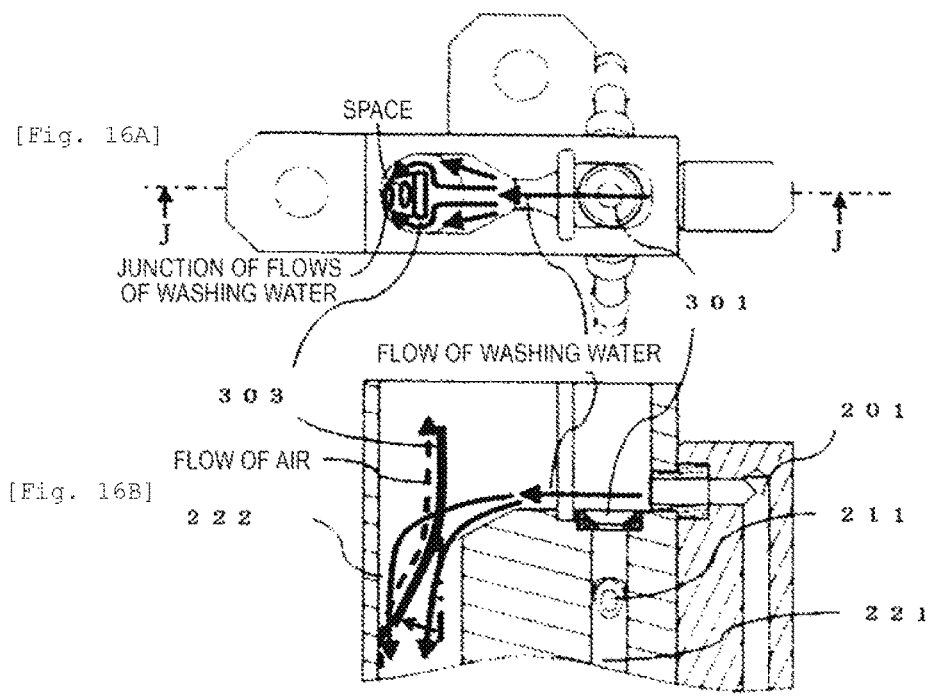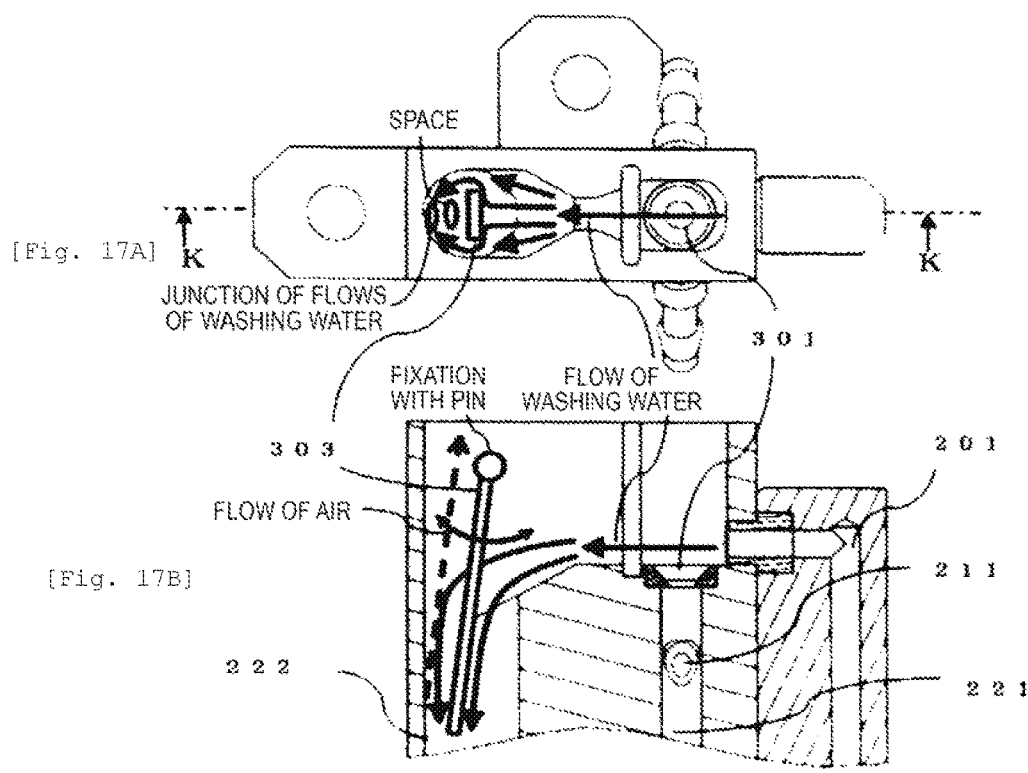

[Fig. 18]
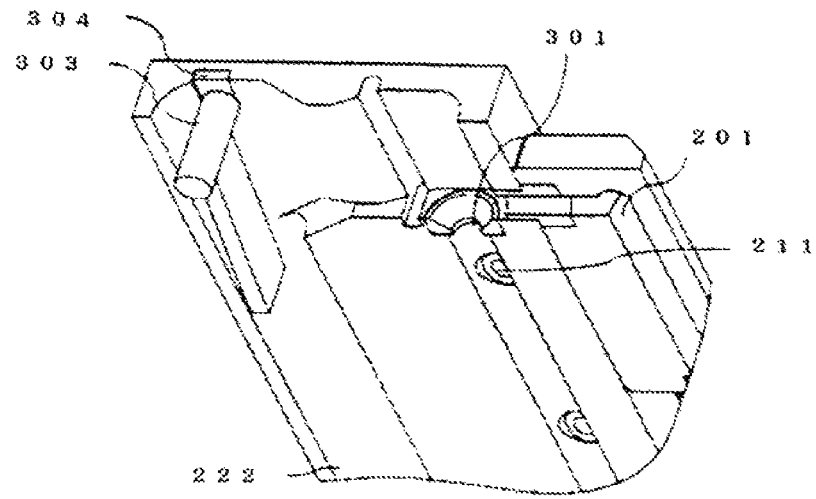
[Fig. 19]
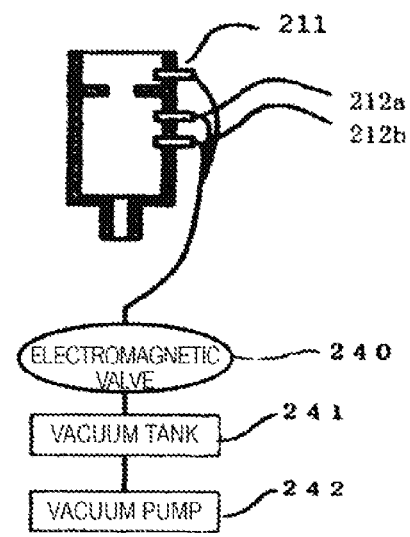

AUTOMATIC ANALYZER

TECHNICAL FIELD

The present invention relates to a dispensing apparatus which dispenses a reagent and a liquid sample such as blood or urine and to an automatic analyzer using the dispensing apparatus.

BACKGROUND ART

Automatic analyzers such as an automatic biochemical analyzer and an automatic immunoassay analyzer, for example, have a washing tank for washing a probe with washing water after the suction and discharge of a reagent or a target specimen sample.

In general, the range of contamination of a probe during the suction of a reagent or a target specimen sample with the probe is about 5 mm, which is the depth to which the probe's tip is thrust into the liquid after detecting the liquid surface, and the range is the washing range of the probe. However, for example, when the reagent is suctioned from a reagent bottle which is covered with a cap with a cut to prevent the evaporation of the reagent, it is necessary to wash the range of the probe which corresponds to the range from the cap of the reagent bottle to the bottom of the reagent bottle. Thus, the range to be washed should be enlarged.

However, when the washing range of the nozzle is enlarged, a longer washing period should be provided. Also, after the probe is washed, a large amount of washing water remains on the surface of the probe. When the next reagent is suctioned with the probe in this state, it is supposed that the washing water remaining on the probe surface contaminates the reagent bottle, and the reagent is sometimes diluted with the washing water. Also in case in which the probe is thrust deep into the target specimen sample, the same problem arises when a broad range of the probe is washed.

Accordingly, when the washing range of the probe is broad (for example, when the washing range is 80 mm from the tip), a method for removing the washing water remaining on the probe surface by moving the probe to the position of a vacuum-suction tube after washing the probe at a probe-washing position, lowering the probe into the vacuum-suction tube and creating a vacuum in the vacuum-suction tube is known as a method for removing the washing water remaining on the probe surface after washing the probe.

However, to increase the speed of the apparatus or to minimize the installation space of the washing tank, methods in which operations of from washing of the probe to drying of the probe are conducted in a single washing tank are known (see PTLs 1, 2 and 3).

CITATION LIST

Patent Literature

PTL 1: JP-A-2002-340913
PTL 2: JP-A-2001-133466
PTL 3: JP-A-2005-257491

SUMMARY OF INVENTION

Technical Problem

In the washing tanks described in PTLs 1 to 3, the diameter of the hole through which the reagent nozzle is inserted is as small as possible to improve the drying effect, and the washing water used for washing the outside of the reagent nozzle is drained through a hole provided separately.

When the pressure of the washing water discharged is low or when the diameter of the drainage flow path is large enough, the washing water to be drained flows along the inner wall of the flow path and is drained before the washing tank overflows.

In order to improve the effect of washing the reagent probe, however, it is necessary to increase the pressure of the washing water for washing the reagent probe. Thus, the flow velocity and the flow rate of the washing water increase, and the waste water floods into the outlet. Therefore, when the washing water cannot be drained efficiently, the washing water used for washing the probe may overflow in the washing tank.

When the washing water used for washing the probe in the washing tank cannot be drained efficiently and thus flows backward, the washing water adheres to the probe to a height above the original height, and the washing water cannot be removed by vacuum-suction. In other cases, when the washing water used for washing the probe adheres to the probe again, the reagent may be diluted or contaminated with the remaining washing water. Therefore, to prevent the backflow of the washing water, it is necessary to drain the washing water used for washing the reagent nozzle efficiently.

The backflow of the washing water can be prevented when the diameter of the outlet could be made large enough; however, there is a limit to the diameter of the outlet because it is required to reduce the size of the washing tank. As the washing water cannot be drained efficiently with the conventional techniques, it has been difficult to further increase the flow velocity and the flow rate of the water for washing the reagent or sample probe and improve the washing effect.

An object of the invention is to develop an automatic analyzer having a washing tank from which the water for washing the reagent or sample probe can be drained efficiently and which is capable of further increasing the flow velocity and the flow rate of the water for washing the reagent or sample probe and improving the washing effect.

Solution to Problem

To achieve the object, the configurations of the invention are as follows.

The automatic analyzer of the invention has: a probe that suctions a reagent or a sample and discharges the reagent or the sample into a reaction container; a dispensing mechanism that moves the probe vertically and horizontally; a suction and discharge mechanism that causes the probe to suction the reagent or the sample and discharge the reagent or the sample into the reaction container; a photometer that analyzes the sample in the reaction container; a washing tank that has an opening into which the probe is inserted and that washes the probe inserted through the opening; and a controller that controls operations of the dispensing mechanism, the discharge mechanism, the photometer and the washing tank.

The washing tank has: a washing portion for washing the probe inserted through the opening; a washing nozzle that discharges washing water to the opening; a suction nozzle that suctions air from the washing portion; an overflow portion through which the washing water discharged from the washing nozzle to the opening drains downward; and a vent member that has a smaller width than the opening size of the overflow portion and that extends from an upper part to a lower part in the overflow portion.

Advantageous Effects of Invention

According to the invention, an automatic analyzer having a washing tank from which the water for washing the reagent or sample probe can be drained efficiently and which is capable of further increasing the flow velocity and the flow rate of the water for washing the reagent or sample probe and improving the washing effect can be developed.

BRIEF DESCRIPTION OF DRAWINGS

FIG. 1 A schematic view of the structure of Example 1 of the invention

FIG. 2 A schematic view of the structure of an automatic analyzer to which the invention is applied FIG. 3 A schematic view of the structure of a washing tank which is partially different from the invention FIG. 4 A figure showing the flow of the washing water in the washing tank shown in FIG. 3

FIG. 5 A figure showing the flow of the washing water in the washing tank shown in FIG. 3, where the washing water is overflowing FIG. 6 A partial oblique cutaway figure showing an example of how the vent plate is attached in Example 1 of the invention FIG. 7 A schematic view of the structure of Example 2 of the invention FIG. 8 A partial oblique cutaway figure showing an example of how the vent plate is attached according to Example 2 of the invention FIG. 9 A schematic view of the structure of Example 3 of the invention FIG. 10 A partial oblique cutaway figure showing an example of how the vent plate is attached according to Example 3 of the invention FIG. 11 A schematic view of the structure of Example 4 of the invention FIG. 12 A partial oblique cutaway figure showing an example of how the vent plate is attached according to Example 4 of the invention FIG. 13 A schematic view of the structure of Example 5 of the invention FIG. 14 A schematic view of the structure of Example 6 of the invention FIG. 15 A schematic view of the structure of Example 7 of the invention FIG. 16 A schematic view of the structure of Example 8 of the invention FIG. 17 A schematic view of the structure of Example 9 of the invention FIG. 18 A partial oblique cutaway figure showing an example of how the vent plate is attached according to Example 9 of the invention FIG. 19 A figure showing an example of the mechanism for conducting the suction with the suction nozzle in the invention

DESCRIPTION OF EMBODIMENTS

Embodiments of the invention are explained below referring to the attached drawings.

EXAMPLES

Example 1

FIG. 1 is a figure including a partial sectional view and the top view of the probe-washing tank in Example 1 of the invention. FIG. 2 is a schematic view of the overall structure of an automatic analyzer to which the washing tank of Example 1 of the invention is applied.

In FIG. 2, reaction containers 2 are arranged circumferentially on a reaction disk 1. Reagent bottles 10 can be placed circumferentially in a reagent disk 9. Also, a detergent bottle 10a can be provided in the reagent disk 9. A sample transportation mechanism 17, which transports a rack 16 carrying sample containers 15, is provided near the reaction disk 1.

Reagent-dispensing mechanisms 7 and 8, which can rotate and move vertically, are provided between the reaction disk land the reagent disk 9, and the reagent-dispensing mechanisms 7 and 8 each have a reagent probe 7a. A reagent syringe 18 is connected to the reagent probes 7a.

A sample-dispensing mechanism 11, which can rotate and move vertically, is provided between the reaction disk 1 and the sample transportation mechanism 17, and the sample-dispensing mechanism 11 has a sample probe 11a.

A sample syringe 19 is connected to the sample probe 11a. The sample probe 11a moves, drawing an arc with a rotation axis for its center, and dispenses the sample in a sample container 15 to a reaction cell (reaction container) 2.

A washing mechanism 3, a spectrophotometer 4, stirring mechanisms 5 and 6, the reagent disk 9 and the sample transportation mechanism 17 are provided around the reaction disk 1, and a washing pump 20 is connected to the washing mechanism 3. A washing tank 13 for the sample probe 11a of the sample-dispensing mechanism 11, 30 and 31 for the stirring mechanisms 5 and 6 and washing tanks 32 and 33 for the reagent probes 7a are provided on the working ranges of the reagent-dispensing mechanisms 7 and 8, the sample-dispensing mechanism 11 and the stirring mechanisms 5 and 6, respectively. The sample containers 15 contain test samples such as blood, and the sample containers 15 on the rack 16 are transported by the sample transportation mechanism 17. The mechanisms are connected to a controller 21, and the operations are controlled by the controller 21.

The sample to be tested in a sample container 15 is dispensed to a reaction cell 2 by the sample probe 11a, and the reagent in a reagent bottle 10 is also dispensed to the reaction cell 2 by the reagent probe 7a. The sample and the reagent are stirred in the reaction cell 2 by the stirring mechanisms 5 and 6. Light emitted from a light source is applied to the mixture solution of the sample and the reagent, and the spectrophotometer 4 receives the light applied. The controller 21 calculates the concentration of a certain component contained in the sample from the intensity of the light received. By such a method, the sample is analyzed.

The above configuration is a general configuration of an automatic analyzer.

Next, referring to FIG. 3 to FIG. 5, an example of a washing tank which is partially the same as Example 1 of the invention but in which the main part is different from those of the Examples of the invention is explained to compare the example with the invention.

The oblique sectional view of the washing tank shown in FIG. 3 shows a structure in which an electromagnetic valve 302 is provided below a waste liquid portion 221.

The structure having the shape shown in FIG. 3 (excluding the electromagnetic valve 302) and a structure having the symmetrical shape to the structure form the washing tank. In this regard, however, the suction nozzle 211 described below is provided on only one of the structures.

In FIG. 3, to wash the reagent probe 7a, the reagent probe 7a is lowered toward the washing tank, and after passing through an opening 311 formed in the upper surface of the washing tank and a throttle portion 301 forming a circular opening, the reagent probe 7a is inserted into the washing tank. A washing nozzle 201 is connected to the opening 311 of the washing tank. As shown in FIG. 5, a flow path throttle portion 305 is provided in the opening 311. That is, the throttle portion 301 forms a flow path in which the washing water discharged from the washing nozzle 201 flows horizontally, and due to the flow path throttle portion 305, the downstream part of the flow path from the throttle portion 301 is narrower than the upstream part of the flow path. Because the part of the flow path is narrow, a part of the washing water discharged from the washing nozzle 201 is easily stored in the throttle portion 301, and the washing water discharged from the inside of the reagent probe 7a inserted to the throttle portion 301 can be effectively prevented from scattering around from the washing tank. The stored washing water is drained downward from the throttle portion 301 as the time elapses, but while the washing water is stored, the layer of the stored washing water functions as a lid which effectively prevents the washing water from scattering around from the washing tank.

A washing portion 205 for washing the reagent probe 7a is provided under the opening 311. A washing nozzle 202 is connected to the washing portion 205.

The washing water is supplied from the washing nozzle 202 to the washing portion 205 in the washing tank, and the washing water is applied to the reagent probe 7a to wash the reagent probe 7a. During this operation, the electromagnetic valve 302 is open. After the reagent probe 7a is washed, the electromagnetic valve 302 under the waste liquid portion 221 is closed, and vacuum nozzles 212a, 212b and 212c connected to the washing portion 205 in the washing tank and a vacuum nozzle 211 connected to the opening 311 start vacuum-suctioning. The reagent probe 7a is raised during the vacuum-suction.

Here, because the vacuum nozzles 212a, 212b and 212c suction air and thus remove the washing water on the reagent probe 7a, the opening of the throttle portion 301 is desirably as narrow as possible from the viewpoint of the improvement of the drying property. When the opening is narrow, however, it is supposed that the reagent scatters around the throttle portion 301 while the reagent probe 7a is lowered in the washing tank, and it is thus necessary to wash the upper surface of the throttle portion 301 with the washing water. Therefore, the flow path of the washing water between the washing nozzle 201 and an overflow portion 222 is configured to be narrow with the flow path throttle portion 305 so that a certain amount of the washing water stays on the throttle portion 301, and this configuration allows washing of the throttle portion 301. In this regard, for convenience, the number of the vacuum nozzles is four (211, 212a, 212b and 212c), but the number of the vacuum nozzles does not have influence because the balance with the vacuum force is involved. Also, as another example, separate flow paths may be provided for the washing water from the washing nozzle 201 and that from the washing nozzle 202, and the pressures of the washing water may be different from each other.

When the electromagnetic valve 302 is closed, air enters the washing tank only from the throttle portion 301. Since the inside diameter of the throttle portion 301 is small, the air which has entered from the throttle portion 301 blows off the washing water remaining on the reagent probe 7a and removes the washing water.

The washing water is supplied to the washing nozzles 201 and 202 from the washing pump 20.

As shown in FIG. 19, the vacuum nozzles 211, 212a and 212b are connected to an electromagnetic valve 240, a vacuum tank 241 and a vacuum pump 242. The inside of the vacuum tank 241 is vacuum-suctioned by the vacuum pump 242, and the vacuum nozzles 211, 212a and 212b vacuum-suction the inside of the washing tank when the electromagnetic valve 240 is opened.

The operations of the electromagnetic valve 240, the vacuum tank 241 and the vacuum pump 242 are controlled by the controller 21.

The vacuum nozzle 212c is not shown in FIG. 19 to simplify the figure.

FIG. 4 is a figure including the top view of the washing tank and a partial sectional view along line B-B, where the washing nozzle is the washing nozzle 201 only, and FIG. 4 shows the flow of the washing water used for washing the reagent probe 7a. In FIG. 4, after washing the reagent probe 7a, the washing water discharged from the washing nozzle 201 spreads from the throttle portion around the center, flows along the slope into the overflow portion 222 and is then drained. When the diameter of the overflow portion 222 is large enough relative to the amount of the washing water, the washing water is drained through the overflow portion 222. However, when the diameter of the overflow portion 222 is made large enough, the washing tank becomes large, which is not preferable.

In addition, it is necessary to increase the pressure of the washing water and wash the reagent probe 7a with a higher amount of water in order to wash the reagent probe 7a sufficiently in a short time. As a result, the washing water floods into the overflow portion 222. The washing water cannot be drained through the overflow portion 222, and the washing water used for washing the probe 7a may overflow in the washing tank as shown in FIG. 5.

As shown in FIG. 5, when the pressure of the washing water discharged from the washing nozzle 201 is increased and the reagent probe 7a is washed with the washing water at a higher flow rate, the washing water which flows while spreading from the throttle portion 305 provided around the center of the washing tank completely covers the overflow portion 222. When the washing water covers the overflow portion 222 and flows in without any space, air remaining in the overflow portion 222 cannot escape and is trapped, and air bubbles are generated.

As shown in FIG. 5, when layers of the washing water alternate with layers of the air bubbles, which are created by the films of the washing water, in the overflow portion 222 and the flow path connected to the overflow portion 222, the entire density of the flow path decreases due to the air bubbles compared to the density of the flow path filled with the washing water.

Here, assuming that the downward pressure exerted on a liquid surface is represented by $\rho gh$ ($\rho$ is the density, g is the gravitational acceleration, and h is the height), the pressure causing the washing water to drain under its own weight decreases as the density $\rho$ reduces. On the other hand, the buoyancy force is exerted on the air bubbles surrounded by the washing water from top and bottom. When the buoyancy force and the force causing the washing water to drain under its own weight balance, the washing water cannot be drained.

For example, when the diameter of the overflow portion 222 is 6 mm, the ratio of the air bubbles and the washing water is 1:1 and the height of the liquid surface is 1 m; the apparent density of the washing water is ½ and the pressure at the liquid surface is about 0.14 N when the friction in the tube and the like are ignored. When the air bubbles account for half of the volume of the tube, the buoyancy force is calculated also at about 0.14 N, which is almost balanced with the pressure, and the drainage is not possible.

Furthermore, when the flow velocity of the washing water is high, the flow of the washing water is split. When the upper flow of the split washing water collides with the inner wall of the washing tank, the washing water swirls in the upper part of the overflow portion 222 and joins the washing water discharged from the washing nozzle 201. As a result, the washing water gathers in the upper part of the overflow portion 222. At this point, since the force by which the washing water drains under its own weight has been reduced, the washing water gathers in the washing tank. When the height of the washing water exceeds the height of the washing water discharged from the washing nozzle 201, the washing water flows backward into the throttle portion 301.

When the washing water used for washing the nozzle overflows in the washing tank, flows backward and adheres to the reagent nozzle 7a, the washing water remains on the reagent nozzle 7a in a part higher than the range to be dried by vacuum-suction. This greatly affects the reliability of the dispensing operation, for example because the reagent is diluted with the washing water brought into the reagent bottle with the reagent probe 7a when the next reagent is suctioned or because the washing water drips down into a neighboring reaction container when the reagent is discharged.

Also, when the washing water used for washing the reagent probe adheres to the reagent probe, the washing water used for washing adheres to the reagent nozzle 7a again. When the reagent probe 7a in this state is inserted into the reagent bottle, the reagent is contaminated or diluted. Moreover, when the washing water overflows the washing tank and spills out in the apparatus, the connectors or the wires may be short-circuited. In order to avoid the risks of the deterioration of the dispensing reliability or apparatus troubles, it is essential to drain the washing water without overflow.

When the washing water flows at a high pressure, the flow velocity of the washing water is high, and the flow is a turbulent flow. After the washing water is discharged from the washing nozzle 201, there are factors which affect the flow such as the reagent nozzle 7a, the difference in level, the throttle around the center and the slope, until the washing water is drained into the overflow portion 222. Depending on the flow of the washing water which flows towards the overflow portion 222, the washing water does not completely cover the overflow portion 222, and the washing water is drained without overflow because a space is created. Thus, the washing water sometimes overflows in the washing tank and sometimes does not.

When the ratio of the amount of the washing water drained and the air bubbles is 6:4, the permissible flow rate of the drainage through the overflow portion 222 with a diameter of 6 mm is about 20.5 mL/s according to the Torricelli's equation.

On the other hand, when the necessary flow rate for washing the reagent probe 7a is about 21 mL/s, the flow rate of the washing liquid flowing into the overflow portion 222 exceeds the permissible flow rate of the overflow portion 222.

Because the flow rate of the washing water cannot be decreased to maintain the capability of washing the reagent probe 7a, the washing water cannot be drained unless the diameter of the overflow portion 222 is increased.

In order to leave a margin of about two times for the permissible flow rate of the overflow portion 222 relative to the flow rate of the washing water, it is necessary that the diameter of the overflow portion 222 is 1.5 times larger or more. However, to actually install the washing tank in the apparatus, the reduction of the size of the washing tank is essential. Thus, the diameter of the overflow portion 222 cannot be increased.

In order to increase the permissible flow rate while maintaining the current diameter of the overflow portion 222, it is essential to remove the air bubbles. When the proportion of the air bubbles is reduced to 10% or less, the permissible flow rate of the overflow portion 222 becomes 31 mL/s or more, and a margin of 1.5 times or more can be left relative to the flow rate of the washing water.

Therefore, in order to drain the washing water efficiently, it is essential to prevent the air bubbles of the sizes which block the overflow portion 222 from being generated in the overflow portion 222.

Next, Example 1 of the invention which is capable of removing the air bubbles from the overflow portion 222 and draining the washing water efficiently is explained referring to FIG. 1 and FIG. 6. FIG. 1 is a figure showing a plane of the washing tank of Example 1 of the invention and the section along line A-A of the plane.

In Example 1 shown in FIG. 1, a vent plate 303 is added to the overflow portion 222 of the washing tank in the example shown in FIG. 4. Although the washing nozzle 202, which supplies the washing water, is not shown in FIG. 1, the washing nozzle 202 is connected to the washing tank as in the example in FIG. 3. Also, the other components are the same as those of the example shown in FIG. 3. Example 1 is applied to the washing tanks 32 and 33.

The washing water discharged from the washing nozzle 201 spreads from the throttle portion 305 at the center and flows into the overflow portion 222. The washing water collides with the vent plate 303 and is divided into right and left flows, in 180-degree opposite directions, at the vent plate 303. The washing water flows between the vent plate 303 and the inner wall of the overflow portion 222, and the flows join behind the vent plate 303.

After joining behind the vent plate 303, the washing water flows downward along the vent plate 303 or the inner wall of the overflow portion 222 and then is drained. At this point, because a space is created between the washing water which has collided with the vent plate 303 and the washing water joined behind the vent plate 303, the washing water can be prevented from completely covering the flow path in the overflow portion 222. Also, since there is a space between the flows of the washing water divided by the vent plate 303, the airflow can be secured during the drainage.

As a result, the air in the overflow portion 222 is released upward (indicated with the dashed arrow in FIG. 1) in exchange for the washing water flowing in the overflow portion 222. When the overflow portion 222 does not contain air bubbles which block the overflow portion 222, the washing water is gradually drained under its own weight.

The horizontal section of the vent plate 303 has a shape which can secure the airflow between the vent plate 303 and the washing water joined behind the vent plate 303. For example, when the vent plate 303 is a solid cylinder, no space is created between the vent plate 303 and the washing water because the overflow portion 222 has a cylindrical shape.

When a vent plate 303 having a width of 5 mm is placed in the middle of an overflow portion 222 having a diameter of 8 mm under the conditions of FIG. 1, a space with a width of 1.5 mm is created at each side of the width direction between the vent plate 303 and the overflow portion 222. The washing water passes through the spaces and flows along the inner wall of the overflow portion 222, and the flows of the washing water join behind the vent plate 303.

When the width of the vent plate is reduced to about 1 mm, however, it is thought that the space between the washing water and the vent plate disappears when the right and left flows of the washing water, which have been divided at the vent plate 303, join. On the contrary, when the width of the vent plate 303 is almost the same as the diameter of the overflow portion 222, the path is divided by the vent plate 303 into a flow path in which the air flows upward and a flow path for draining the washing water, and the permissible flow rate is reduced by half. At this point, when the flow rate of the washing water flowing into the overflow portion 222 exceeds the permissible flow rate of the overflow portion 222, the washing water overflows. Thus, the width of the vent plate 303 is desirably about 50 to 70% of the diameter of the overflow portion 222.

FIG. 6 is a figure showing a specific example of the vent plate 303 shown in FIG. 1. In the example shown in FIG. 6, two grooves 306 are formed in the upper surface part of the washing tank main body which forms the overflow portion 222. The vent plate 303 is a T-shaped plate having parts protruding in two opposite directions in the upper part, and the protruding parts of the vent plate 303 are inserted to the grooves formed in the upper surface part. In addition, a structure in which a cover on which the vent plate 303 is fixed is applied on top of the overflow portion 222 is also acceptable.

It is necessary that the height of the vent plate 303 is above the height of the flow of the washing water, as shown in FIG. 1. Also, a height which the washing water that has collided with the vent plate 303 does not flow over even when the level of a part thereof rises is necessary. For example, in case in which the washing liquid flows with a width of 8 mm and a height, which is indicated by the reference sign 308, of 3 mm and 25% of the flow which collided with the vent plate 303 rises by 3 mm, it is necessary that the height 307 of the vent plate 303 is at least 11 mm from the bottom surface of the flow of the washing water (the surface extended from the upper surface part of the throttle portion 301 at the nozzle-insertion side) in order to leave a margin of 5 mm for the height.

Regarding the length of the vent plate 303, it is necessary that the vent plate 303 extends with enough length to a position below the air bubbles shown in FIG. 5 in order to prevent the washing water from completely covering the overflow portion 222 and trapping the air. When the height 309 of the washing water colliding with the wall of the overflow portion 222 is 20 mm from the lower end of the flow of the washing liquid and the size of the air bubbles is about 10 mm, the minimum length 310 of the vent plate 303 is 40 mm from the lower end of the flow of the washing liquid in order to leave a margin of about 10 mm for the length.

The vent plate 303 is attached at a position a little closer to the throttle portion 301 from the center of the overflow portion 222. For example, when the diameter of the overflow portion 222 is 8 mm and the width of the vent plate 303 is 5 mm, the vent plate 303 is attached at a position about 1 to 2 mm closer to the throttle portion 301 from the center of the overflow portion 222.

This is because a space is created easily between the vent plate 303 and the washing water which has been divided and then joined. When the vent plate 303 is 2 mm or more closer to the throttle portion 301, the level of the washing water which has collided with the vent plate 303 may rise remarkably along the vent plate 303. On the other hand, when the vent plate 303 is placed further from the throttle portion 301, the space may not be created between the vent plate 303 and the washing water.

Accordingly, the position of the vent plate 303 is about 1 to 2 mm closer to the throttle portion 301 from the center of the overflow portion 222.

As described above, according to Example 1 of the invention, it is possible to remove the air bubbles from the overflow portion 222 and drain the washing water efficiently, because the plate-like vent plate 303 with appropriate length and width is provided in an upstream part of the overflow portion 222 and the washing water used for washing the reagent probe 7a is divided and then caused to flow into the overflow portion 222. Also, even when the washing water is discharged from the washing nozzle 201 at a flow rate and a flow velocity which completely cover the overflow portion 222 to trap the air and cause the above problems when the vent plate 303 is not provided, the provision of the vent plate 303 allows washing of the reagent probe 7a without decreasing the flow rate and the flow velocity and allows efficient drainage of the washing water.

Accordingly, an automatic analyzer having a washing tank from which the water for washing the reagent probe can be drained efficiently and which is capable of further increasing the flow velocity and the flow rate of the water for washing the reagent probe and improving the washing effect can be developed.

Example 2

FIG. 7 is a figure including the top view of the probe-washing tank according to Example 2 of the invention and a partial sectional view along line C-C.

In Example 2 shown in FIG. 7, the vent plate 303 is a hollow cylinder from which a part at which the flows of the washing water join has been cut off (an approximately C-shaped cross-section). The shape of the cross-section may be a semicircle. The flow of the washing water is divided along the shape of the vent plate 303, and the flows join behind the vent plate 303. Because the cross-section has a hollow shape such as a cylinder, the airflow is secured more easily.

Advantages of the example shown in FIG. 7 are that the washing water can be divided smoothly and the airflow is secured easily since the cross-section of the vent plate 303 has a hollow circular shape. Polygons such as a triangle, a square and a trapezoid also have the same advantages. The position and the height of the vent plate 303 in FIG. 7 and the like are the same as those in FIG. 1. Also, the other components are the same as those of the example shown in FIG. 1. An example of how the vent plate 303 in FIG. 7 is attached is shown in FIG. 8. That is, an attachment plate 303a for attaching the vent plate 303 to the overflow portion 222 is provided in the upper part of the vent plate 303, and by attaching the attachment plate 303a to the opening of the overflow portion 222, the vent plate 303 can be attached to the overflow portion 222. In this regard, an air hole may be formed in the upper surface of the attachment plate 303a to secure the path of the air flowing from the vent plate 303.

The same effects as those of Example 1 can be obtained also by Example 2 of the invention. Furthermore, Example 2 also has effects of dividing the washing water smoothly and securing the airflow more easily.

Example 3

FIG. 9 is a figure including the top view of the probe-washing tank according to Example 3 of the invention and a partial sectional view along line D-D.

Example 3 shown in FIG. 9 is an example in which the cross-section of the vent plate 303 is a triangle (an approximately V-shaped cross-section) to ventilate easily during the drainage of the washing water. In the example shown in FIG. 9, because the vertex of the triangle faces the flow of the washing water, the flow is divided along the shape of the triangle without any trouble. Also, because the part behind at which the flows of the washing water join is concave as in FIG. 7, the airflow is secured easily. With the triangular cross-section, the washing water is divided more easily than in the example in FIG. 7. The position and the height of the vent plate 303 in FIG. 9 and the like are the same as those in FIG. 1. Also, the other components are the same as those of the example shown in FIG. 1. An example of the attachment in FIG. 9 is shown in FIG. 10. That is, an attachment plate 303b for attaching the vent plate 303 to the overflow portion 222 is provided in the upper part of the vent plate 303, and by attaching the attachment plate 303b to the opening of the overflow portion 222, the vent plate 303 can be attached to the overflow portion 222.

The same effects as those of Example 1 can be obtained also by Example 3 of the invention. Furthermore, Example 3 also has effects of dividing the washing water smoothly and securing the airflow more easily.

Example 4

FIG. 11 is a figure including the top view of the probe-washing tank according to Example 4 of the invention and a partial sectional view along line E-E.

Example 4 shown in FIG. 11 shows an example in which the vent plate 303 shown in FIG. 7 is inverted. In the case of this shape, most of the washing water which flows in is received in the cylinder to create a space behind the cylinder, and the airflow is thus secured. Polygons such as a triangle and a square also have the same effect.

The shape of the example shown in FIG. 11 is effective when the flow of the washing water does not spread and collides with the vent plate 303 together. The height of the vent plate 303 shown in FIG. 11 and the like are the same as those in FIG. 1. Also, the other components are the same as those of the example shown in FIG. 1. With respect to the attachment position in the example in FIG. 11, the vent plate 303 is provided in the middle of the overflow portion 222 since the flow path may become narrow when the vent plate 303 is close to the throttle portion 301 as in FIG. 1 and the like.

An example of the attachment in FIG. 11 is shown in FIG. 12. That is, an attachment plate 303c for attaching the vent plate 303 to the overflow portion 222 is provided in the upper part of the vent plate 303, and by attaching the attachment plate 303c to the opening of the overflow portion 222, the vent plate 303 can be attached to the overflow portion 222.

The same effects as those of Example 1 can be obtained also by Example 4 of the invention. Furthermore, Example 4 also has effects of dividing the washing water smoothly and securing the airflow more easily.

Example 5

FIG. 13 is a figure including the top view of the probe-washing tank according to Example 5 of the invention and a partial sectional view along line F-F.

Example 5 shown in FIG. 13 is an example in which the cross-sectional shape of the vent plate 303 is a cylinder and small holes (perforations) are formed in the wall. Since the cross-sectional shape of the vent plate 303 is a cylinder, the air is released from a lower part of the cylinder portion even when the washing water covers the overflow portion 222, and the generation of air bubbles which block the overflow portion 222 can be prevented.

The cylinder is formed through the vent plate 303 from the upper end to the lower end. Also, by using a hydrophobic material for the vent plate 303 and forming minute holes in the wall of the cylinder, a liquid cannot enter from the holes, and only air can enter the cylinder and can be emitted. While the air can be emitted only from the upper end of the cylinder when the wall of the cylinder does not have the holes, the air can be emitted through the holes in the wall of the cylinder, regardless of the heights of the air bubbles, when holes are formed in the wall in the height direction.

The other components are the same as those of the example shown in FIG. 1.

The same effects as those of Example 1 can be obtained also by Example 5 of the invention. Furthermore, Example 5 also has effects of emitting the air from the holes in the wall of the cylinder and securing the airflow more easily.

Example 6

FIG. 14 is a figure including the top view of the probe-washing tank according to Example 6 of the invention and a partial sectional view along line G-G.

Example 6 shown in FIG. 14 is an example in which the vent plate 303 is integrated into the washing tank. In FIG. 14, the vent plate 303 is integrated into the inner wall of the overflow portion 222, and the flow path for the ventilation and the flow path for the drainage are separated. The cross-sectional shape of the vent plate 303 in FIG. 14 may be a polygon such as a triangle.

By integrating the vent plate 303 into the washing tank, the space for the ventilation can be secured certainly. Thus, the washing water can be drained smoothly even when the flow rate is high. Also, when the vent plate 303 is integrated into the washing tank, the number of the parts can be reduced.

Furthermore, by forming holes in the wall of the vent plate 303 as in the example shown in FIG. 13 and using a hydrophobic material, the same effects as those of the example in FIG. 13 are obtained.

The height of the vent plate 303 in FIG. 14 is the same as that in FIG. 1. Also, the other components are the same as those of the example shown in FIG. 1.

The same effects as those of Example 1 can be obtained also by Example 6 of the invention. Furthermore, Example 6 has not only an effect of draining the washing water smoothly even when the flow rate is high but also an effect of reducing the number of the parts since the vent plate 303 is integrated into the washing tank.

Example 7

FIG. 15 is a figure including the top view of the probe-washing tank according to Example 7 of the invention and a partial sectional view along line H-H.

Example 7 shown in FIG. 15 is an example in which a triangular vent plate is integrated into the slope of the washing tank and in which the air is emitted through the concave part in the triangle. Because the washing water is divided before flowing into the overflow portion 222, the ventilation is easier with this structure.

In the example shown in FIG. 15, because the flow path of the air is closer to the throttle portion 301 than to the overflow portion 222, the washing water can be drained smoothly even when the flow rate is high and the flow velocity is high. The cross-sectional shape of the vent plate 303 may also be an arc or a polygon. The height of the vent plate 303 in FIG. 15 is the same as that in FIG. 1. Also, the other components are the same as those of the example shown in FIG. 1.

The same effects as those of Example 1 can be obtained also by Example 7 of the invention. Furthermore, Example 7 has not only an effect of draining the washing water smoothly even when the flow rate is high but also an effect of reducing the number of the parts since the vent plate 303 is integrated into the washing tank.

Example 8

FIG. 16 is a figure including the top view of the probe-washing tank according to Example 8 of the invention and a partial sectional view along line J-J.

Although the vent plate 303 is provided vertically in the examples in FIG. 6 to FIG. 15 described above, it is thought that the washing water is drained more easily in the actual apparatus when the vent plate 303 is inclined.

Example 8 of the invention is an example taking the above issue into consideration, and the material of the vent plate 303 is elastic (elastic member) in this example.

In FIG. 16, when the pressure of the washing water from the washing nozzle 201 is increased to improve the washing effect, the velocity of the flow colliding with the vent plate 303 increases as well. When the vent plate 303 is provided vertically, the washing water may scatter upward. Thus, in case in which the material of the vent plate 303 is elastic, the vent plate 303 bends when the washing water collides with the vent plate 303, and the power of the washing water can be absorbed. Because the vent plate 303 bends, the washing water is caused to flow downward after colliding with the vent plate 303 and is drained easily, and the washing water can be prevented from scattering upward.

As the flow velocity of the washing water from the washing nozzle 201 becomes high, the degree of the bend of the vent plate 303 becomes large, and the flow of the washing water can be caused to be further downward. The position and the height of the vent plate 303 in FIG. 16 and the like are the same as those in FIG. 1. Also, the other components are the same as those of the example shown in FIG. 1.

The same effects as those of Example 1 can be obtained also by Example 8 of the invention. Furthermore, Example 8 also has an effect of preventing the washing water from scattering upward by causing the washing water to flow downward after colliding with the vent plate 303 and to drain easily and an effect of draining the washing water smoothly even when the flow rate is high.

Example 9

FIG. 17 is a figure including the top view of the probe-washing tank according to Example 9 of the invention and a partial sectional view along line K-K.

Example 9 shown in FIG. 17 is an example in which the support of the vent plate 303 is pinned support. That is, the way of supporting the vent plate 303 is support with a pin which allows the vent plate 303 to rotate. By supporting one end of the vent plate 303 with a pin 304 and allowing the vent plate 303 to rotate, the vent plate 303 inclines depending on the flow velocity of the washing water, and the washing water can be caused to flow further downward. Also, because the vent plate 303 rotates, the load applied to the vent plate 303 can be reduced compared to the example in FIG. 16. The position and the height of the vent plate 303 in FIG. 17 and the like are the same as those in FIG. 1. An example of the attachment in FIG. 17 is shown in FIG. 18. That is, the vent plate 303 can be attached to the washing tank with the pin 304.

The position and the height of the vent plate 303 in FIG. 17 and the like are the same as those in FIG. 1. Also, the other components are the same as those of the example shown in FIG. 1.

The same effects as those of Example 1 can be obtained also by Example 9 of the invention. Furthermore, Example 9 also has an effect of preventing the washing water from scattering upward by causing the washing water to flow downward after colliding with the vent plate 303 and to drain easily and an effect of draining the washing water smoothly even when the flow rate is high.

Although the washing tank according to the invention has been described with respect to the reagent probe, in another dispensing style, the sample probe is thrust deep into the specimen in the sample container 15 to suction the sample from the bottom of the sample container 15. The washing range of the probe can be applied not only to the reagent probe but also to the sample probe, and the invention can be applied to a wide range of washing tanks.

Accordingly, the washing tank of the invention is not limited to one for a reagent probe only, but the washing tank is effective for conducting the operations of from washing to drying at the same position and washing a probe which should be washed over a wide range.

In addition, the invention can be achieved not only as an automatic analyzer having the above washing tank but also as the washing tank alone. This is because the washing tank alone can be manufactured and sold.

In the present description, representative examples of the washing tank of the invention have been explained using FIG. 1 and FIG. 3, but the invention is not limited to these specific examples. That is, because the probe is sometimes washed sufficiently with the washing nozzle 201, the washing nozzle 202 is not an essential component. Also, because vacuum-suction (drying) is sometimes sufficient with the suction nozzle 212a or the like, the suction nozzle 211 is not an essential component. In the washing tank according to the invention, at least the washing nozzle 201 and the suction nozzle 212a should be provided.

REFERENCE SIGNS LIST

1 ... Reaction disk, 2 ... reaction container, 3 ... washing mechanism, 4 ... spectrophotometer, 5 and 6 ... stirring mechanisms, 7 and 8 . . . reagent-dispensing mechanisms, 7a . . . reagent probe, 9 . . . reagent disk, 10 . . . reagent bottle, 10a . . . detergent bottle, 11 . . . sample-dispensing mechanism, 11a . . . sample probe, 13 . . . washing tank for sample-dispensing mechanism, 15 . . . sample container, 16 . . . rack, 17 . . . sample transportation mechanism, 18 . . . reagent syringe, 19 . . . sample syringe, 20 . . . washing pump, 21 . . . controller, 30 and 31 . . . washing tanks for stirring mechanisms, 32 and 33 . . . washing tanks for reagent-dispensing mechanisms, 201 and 202 . . . washing nozzles, 211, 212a, 212b and 212c . . . suction nozzles, 221 . . . waste liquid portion, 222 . . . overflow portion, 301 . . . throttle portion, 302 . . . electromagnetic valve, 303 . . . vent plate, 304 . . . fixation pin, 305 . . . flow path throttle portion, 306 . . . groove, and 311 . . . opening.

The invention claimed is:

1. An automatic analyzer comprising:
a probe that suctions a reagent or a sample and discharges the reagent or the sample into a reaction container,
a dispensing mechanism that moves the probe vertically and horizontally,
a suction and discharge mechanism that causes the probe to suction the reagent or the sample and discharge the reagent or the sample into the reaction container,
a photometer that analyzes the sample in the reaction container,
a washing tank that has a first opening into which the probe is inserted and that washes the probe inserted through the opening, and
a controller that controls operations of the dispensing mechanism, the discharge mechanism, the photometer and the washing tank,
wherein the washing tank comprises:
a washing portion for washing the probe inserted through the first opening,
a first washing nozzle that discharges washing water to the first opening,
a suction nozzle that suctions air from the washing portion,
an overflow portion that has a second opening through which the washing water discharged from the first washing nozzle to the first opening drains downward, and
a vent plate attached to the overflow portion and that has a smaller width than an opening size of the second opening of the overflow portion, and that is disposed to extend within the overflow portion through the second opening from an upper part to a lower part of the overflow portion.

2. The automatic analyzer according to claim 1, wherein:
the washing tank further comprises a throttle portion which has a smaller diameter than an opening size of the first opening and which is provided between the first opening and the washing portion, wherein the probe is inserted into the throttle portion,
the first washing nozzle supplies the washing water to the first opening from the side, and
the washing water discharged from the first washing nozzle collides with the vent plate and is introduced to the overflow portion by the vent member.

3. The automatic analyzer according to claim 1, wherein the vent plate has an approximately C-shaped cross-section.

4. The automatic analyzer according to claim 1, wherein the vent plate has an approximately V-shaped cross-section.

5. The automatic analyzer according to claim 3, wherein the vent plate is integrated into the overflow portion.

6. The automatic analyzer according to claim 4, wherein the vent plate is integrated into the overflow portion.

7. The automatic analyzer according to claim 1, wherein the vent plate is an elastic member.

8. The automatic analyzer according to claim 1, wherein an end of the vent plate is rotatably supported on the overflow portion.

9. An automatic analyzer comprising:
a probe that suctions a reagent or a sample and discharges the reagent or the sample into a reaction container,
a dispensing mechanism that moves the probe vertically and horizontally,
a suction and discharge mechanism that causes the probe to suction the reagent or the sample and discharge the reagent or the sample into the reaction container,
a photometer that analyzes the sample in the reaction container,
a washing tank that has a first opening into which the probe is inserted and that washes the probe inserted through the opening, and
a controller that controls operations of the dispensing mechanism, the discharge mechanism, the photometer and the washing tank,
wherein the washing tank comprises:
a washing portion for washing the probe inserted through the first opening,
a first washing nozzle that discharges washing water to the first opening,
a suction nozzle that suctions air from the washing portion,
an overflow portion that has a second opening through which the washing water discharged from the first washing nozzle to the first opening drains downward, and
a cylindrical vent member attached to the overflow portion and that has a smaller width than an opening size of the second opening of the overflow portion, and that is disposed to extend within the overflow portion through the second opening from an upper part to a lower part of the overflow portion,
wherein the vent member has perforations in a side face thereof.

* * * * *